United States Patent
Chang et al.

(12)

(10) Patent No.: US 11,207,366 B2
(45) Date of Patent: Dec. 28, 2021

(54) TRADITIONAL CHINESE MEDICINE COMPOSITION COMPRISING DRIED TANGERINE PEELS AND DARK TEA FOR TREATING DIABETES AND PREPARATION METHOD THEREOF

(71) Applicants: Guosheng Chang, Guangzhou (CN); Fengcan Jiang, Guangzhou (CN)

(72) Inventors: Guosheng Chang, Guangzhou (CN); Fengcan Jiang, Guangzhou (CN)

(*) Notice: Subject to any disclaimer, the term of this patent is extended or adjusted under 35 U.S.C. 154(b) by 47 days.

(21) Appl. No.: 16/317,621

(22) PCT Filed: Nov. 10, 2017

(86) PCT No.: PCT/CN2017/110339
§ 371 (c)(1),
(2) Date: Jan. 14, 2019

(87) PCT Pub. No.: WO2018/214412
PCT Pub. Date: Nov. 29, 2018

(65) Prior Publication Data
US 2019/0231839 A1    Aug. 1, 2019

(30) Foreign Application Priority Data

May 24, 2017 (CN) .......................... 201710372286.X
May 24, 2017 (CN) ............................ 201710372319.0
May 24, 2017 (CN) ............................ 201710372340.0
May 24, 2017 (CN) ............................ 201710372508.8

(51) Int. Cl.
| | | |
|---|---|---|
| A61K 36/752 | (2006.01) |
| A61K 36/82 | (2006.01) |
| A61P 3/10 | (2006.01) |
| A23F 3/14 | (2006.01) |
| A23L 19/00 | (2016.01) |
| A23F 3/08 | (2006.01) |

(52) U.S. Cl.
CPC .............. *A61K 36/752* (2013.01); *A23F 3/14* (2013.01); *A61K 36/82* (2013.01); *A61P 3/10* (2018.01); *A23F 3/08* (2013.01); *A23L 19/09* (2016.08)

(58) Field of Classification Search
None
See application file for complete search history.

(56) References Cited

FOREIGN PATENT DOCUMENTS

| CN | 1830279 A | 9/2006 |
| CN | 101558801 A | * 10/2009 |
| CN | 102960491 A | 3/2013 |
| CN | 106177432 A | * 12/2016 |

OTHER PUBLICATIONS 2015, https://www.twodogteablog.com/tag/ganpu/.*
Ma Sen. "Study on the Effect of Reducing Blood Glucose of the Peels of Citrus Suavissima and Orange", Journal Ofwuyi University, vol. 29, No. 2, Apr. 30, 2010, p. 18-20 (English abstract is attached).
International Search Report of PCT/CN2017/110339, dated Feb. 26, 2018.
Written Opinion of the International Search Authority of PCT/CN2017/110339, dated Feb. 26, 2018.

* cited by examiner

*Primary Examiner* — Terry A McKelvey
*Assistant Examiner* — Catheryne Chen
(74) *Attorney, Agent, or Firm* — CUSPA Technology Law Associates, P.A.; Yi Li

(57) ABSTRACT

A traditional Chinese medicine composition for treating diabetes and a preparation method thereof, the composition comprises dried tangerine peels and dark tea. The preparation method utilizes Pu'er tea to shuffle placement with the dried tangerine peels to preserve the dried tangerine peels, mixes different kinds of dried tangerine peels of different aging years, adds the mixed dried tangerine peels with pile-fermented black tea, presses the mixed black tea into tea bricks, and secondarily-ferments the tea bricks, then ages the secondary fermented tea bricks for two years.

9 Claims, No Drawings

TRADITIONAL CHINESE MEDICINE COMPOSITION COMPRISING DRIED TANGERINE PEELS AND DARK TEA FOR TREATING DIABETES AND PREPARATION METHOD THEREOF

TECHNICAL FIELD

The present invention relates to a traditional Chinese medicine composition for treating diabetes and a preparation method thereof, and more particularly to a traditional Chinese medicine composition comprising dried tangerine peels and dark tea as main ingredients for treating diabetes and a preparation method thereof.

BACKGROUND OF THE INVENTION

Diabetes has been one of the major diseases threatening human health. According to The WHO, the number of global diabetic patients has reached to about 400 millions, accounting for 6% of the world's total population. Among the 400 millions diabetic patients in the world, China takes about 110 million, accounting for 8% of the China's total population. Thus China is the country with the largest number of diabetic patients and a higher incidence of diabetes in the world. Because the number of diabetic patients increases rapidly both in the world and China, it is an urgent task for the pharmaceutical industry to invent better medicines to suppress increase in diabetic patients.

Diabetes is a basic disease, which may impair various major organs, resulting in complications of heart disease, stroke, nerve injury, renal failure, impotence, limbs infection, etc.

Due to urgency and severity of diabetes, all countries attach importance to developing new drugs for treating the disease. The main drugs for treating it currently are basically chemical drugs such as insulin, acarbose, pioglitazone, glipizide, glimepiride, metformin, etc. However, the efficacy of these chemical drugs is different for different patients. For example, metformin is more suitable for fat patients, while it is preferred to administrate acarbose to patients with a thin physique. Therefore, clinically, selection of drugs should be in accordance with physical conditions, illness conditions and sensitivity to a particular drug, that is, individual difference of a patient. Now the commonly-used drugs for treating diabetes are lack of a broad spectrum.

In addition, most of the chemical drugs have greater side effects in comparison with natural herb medicines. For example, metformin can damage to the stomach, and acarbose can impair liver. Thus, doctors have to distinguish patient conditions and be carefully in clinical application of chemical medicines.

Insulin is an effective drug to treat diabetes, but the dosage of insulin needs to be adjusted according to the level of the blood glucose value at the injection time. Further, it is inconvenient to take insulin when going on a trip because insulin needs to be refrigerated.

The treatment of diabetes by using the traditional Chinese medicines is just stayed at the stage of symptomatic treatment rather than radical treatment. The treatment mainly focuses on the symptoms and complications of diabetes. For example, diabetes is referred to as "XiaoKe" symptom, meaning thirsty symptom, in traditional Chinese medicine. Therefore, the treatment aims at eliminating the symptoms such as thirsty or laryngoxerosis. Furthermore, the diabetic patients show symptoms of polyphagia and polyuria, because of that, traditional Chinese medicine theory holds it is the problem of kidney, and polyphagia and polyuria reflect the deficiency of the performance of kidney, for the kidney controlling water metabolism in the body. So nourishing kidney is usually adopted as the way of treatment. In addition, traditional Chinese medicine thinks the diabetes is because of either deficiency of "qi", meaning vitality of energy and spirit, and "yin", one of the healthy balancing element, or deficiency of "qi" and "yang", the opposite balancing element of "yin". Therefore, a prescription of nourishing liver and kidney and activating blood circulation is often used to treat diabetic nephropathy patients with deficiency of qi and yin. Traditional Chinese medicine believes that diabetic cardiopathy is caused by deficiency of qi and yang, so under the traditional Chinese Medicine a prescription of nourishing heart to increase "yang" and of activating blood to promote qi should be adopted. In addition, diabetes used to cause neuropathy. In that case, a prescription of tonifying spleen and stomach is usually used when treating diabetic nerve impaired patients in traditional Chinese medicine.

Different from chemical medicine, which targets blood glucose to treat diabetes, no traditional Chinese medicine recipe, which adopts the method of directly decreasing blood glucose to treat diabetes, up to date. The reason may be that although some single herb or herb-composition recipe in traditional Chinese medicine is effective to reduce blood glucose, the concentration of them is too low to have clinical significance.

China Food and Drug Administration approved and promulgated 35 kinds of traditional Chinese medicines for treating diabetes. Among them, one is an active ingredient extracted from traditional Chinese medicine herb, two are combinations of traditional Chinese medicines and chemical medicines, and the other 32 are traditional Chinese medicine herb-compositions.

Pharmacological researches and clinical tests indicate that these traditional Chinese medicines can reduce blood glucose and improve lipid metabolism to certain extent by regulating functions of associated organs, but the strength of reducing blood glucose of them is much weaker than that of chemical medicines. It is impossible for most diabetic patients to reduce blood glucose to a satisfied level just by using traditional Chinese medicines, excepting for some mild patients in early stage of diabetes.

However, in terms of toxicity, the traditional Chinese medicine is generally known to be less toxic than that of chemical medicines. The side effect of traditional Chinese medicine lies in that the property of traditional Chinese medicine herbs. Chinese medicine theory holds every herb has its inherent characteristics of "cold", "hot", "warm" or "cool", which affects the treatment of a disease. So according to different constitutions, diseases different stages of the disease, different climates and different seasons, the prescription should be changed. That results in inconvenience in administration of traditional Chinese medicine.

Statistics show that it is not optimistic that type II diabetes patients control their blood glucose. Only less than one thirds of the patients control it to a satisfied level. The ratio of the patients whose blood glucose, blood pressure and blood lipids are all well controlled only accounts for 5.6%.

In addition, about 60% of type II diabetes patients suffer from overweight or obesity. The risks of occurrence, development speed and seriousness of diabetic complications are significantly increasing among type II diabetes patients because of the poor control of blood glucose, blood pressure, blood lipids and weight. Therefore, comprehensive management of healthy conditions of diabetic patients has been recommended for treating the disease. The comprehensive management of healthy conditions requires diabetes patients to control all the risky factors of blood glucose, blood pressure, blood lipids and weight at the same time.

At present, the comprehensive management of diabetes symptoms means administrating many different kinds of drugs, because there is not a single chemical drug that has multiple and efficient effects of reducing the abnormal levels of blood glucose, blood pressure, blood lipids and weight at the same time.

In view of the current situations of diabetes treatment, it is necessary to develop a new diabetic drug with low toxic side effects, convenient administration, a broad spectrum and multiple effects.

SUMMARY OF THE INVENTION

Definition

The term "micro fermentation" described herein refers to the processes of "aging", "leaving" or storing, for a period of time, the tea leaves, tea bricks, peels of citrus fruits or the tangerine peels.

The term "fermentation" described herein refers to "pile-fermentation" or "secondary fermentation" (fermentation after the loose dark tea leaves are pressed into tea bricks), for dark tea.

The term "trans-contamination" described herein refers to the processes of "shuffling placement of dried tangerine peels with Pu'er tea", for Yang Pi (Yang means preservation and Pi means Peels) purpose.

The term "Yang Pi" described herein refers to the process of preserving the dried tangerine peels by shuffling placement of them together with Pu'er tea to age them together for years.

The term of "golden flower" described herein refers to the Eurotiumcristatum, which appears in the secondary fermentation of dark tea.

The term of "blossom of golden flower" described herein refers to the appearance of Eurotiumcristatum in the dark tea brick during the secondary fermentation of dark tea.

The term "peels of citrus fruits" described herein refers to the skins of oranges aged for less than 3 years.

The term "dried tangerine peels" described herein refers to the "peels of citrus fruits" aged for more than 3 years.

The term "dark tea" described herein is a collective term for secondary fermented tea comprising Pu'er tea, Jinfu tea, Fu tea, Qianliang tea, Bailiang tea, etc. And it also refers to the prepared tea after secondary fermentation.

The term of "black tea" in the invention is referred to the tea leaves when the color of them become dark brown after pile-fermentation.

The term "Shu Pu'er" described herein refers to ripened Pu'er tea.

The term "Sheng Pu'er" described herein refers to un-ripened Pu'er tea.

The term "tea drinks" described herein refers to the tea or tea bags prepared according to the present invention, or the tea water brewed or boiled with the tea or tea bags prepared according to the present invention.

The term "tea brick" described herein refers to all possible shapes of pressed form of tea leaves such as tea brick, tea column, tea ball and tea cake.

The term "brick pressing" described herein refers to the process of pressing tea leaves into a shape of brick, column, ball, cake etc.

The present invention provides a traditional Chinese medicine composition for treating and preventing diabetes.

The present invention provides a non-toxic traditional Chinese medicine composition for treating and preventing diabetes.

The present invention provides a conveniently administrated traditional Chinese medicine composition for treating and preventing diabetes.

The present invention provides a traditional Chinese medicine composition with a broad spectrum for treating and preventing diabetes.

The present invention provides a traditional Chinese medicine composition with multiple effects for treating and preventing diabetes.

The present invention provides a preparation method for a traditional Chinese medicine composition for treating and preventing diabetes.

The dried tangerine peels are made from the peels of citrus fruits. The peels of citrus fruits which are aged for 3 years will be re-named as "dried tangerine peels", and the peels of citrus fruits which are aged for 5 years will start to give out aroma. From the perspective of the aroma and drug effects, the longer the dried tangerine peels are aged, the better. The dried tangerine peels in Guangdong province China are the most authentic, wherein the dried tangerine peels in Xinhui county are the most famous for its best quality. The citrus peels can be classified into green tangerine peels, yellow-green tangerine peels and yellow-red tangerine peels according to the different species of the oranges.

The important effective ingredients of the dried tangerine peels are flavonoids namely, flavonoid, flavanone and flavonol, and most of the flavonoids exist in the form of glucoside. The flavonols of the dried tangerine peels comprise: hesperidin, neohesperidin and nobiletin. Those flavonoids ingredients show significant biological activity in the aspects of anti-oxidation, anti-tumor, decreasing blood glucose and cholesterol, preventing cardiovascular diseases, sedation, anti-inflammation, anti-bacteria, insecticide and anti-platelet aggregation. The testing and analysis results indicate that the flavonoids of the dried tangerine peels are one of the active ingredients to decrease blood glucose, and the total amount of the flavonoids will increase with the aging time.

Chinese tea is generally classified into categories of white tea, green tea, yellow tea, oolong tea, black tea and dark tea. Among the Chinese tea, green tea and white tea are non-fermented tea; yellow tea is mild-fermented tea; oolong tea is semi-fermented tea; black tea is fully-fermented tea; and dark tea is post-fermented tea (secondary fermented tea). The dark tea mainly comprises Yunnan Pu'er tea, Hunan dark tea, Shanxxi Fu tea. The Hunan dark tea can be classified into Fu tea, Jinfu tea, Qianliang tea and Bailiang tea according to different processing methods. The Fu tea will be called Jinfu tea after "blossom of golden flower" (appearance of Eurotiumcristatum). Dark tea in Hunan province, especially in Anhua county, is the most famous of its best quality.

Dark tea can regulate blood lipids. As described in the six volume of "BencaoGangmuShiyi" (a medical book) authored by ZhaoXuemin in Qing dynasty, "Pu'er tea is applied to eliminate phlegm, help digest greasy food, and loose the bowels to relieve constipation". From the above description, it can be concluded that Pu'er tea started to be used for health care and treatment of disease from very ancient time in China.

Studies indicate that there are a lot of useful and effective ingredients in Pu'er tea. For instance, tea polysaccharide has effects on protecting hepatic steatosis, while the content of tea polysaccharide in Shu Pu'er tea (ripened Pu'er tea) is 6.86 times higher than that of Sheng Pu'er tea (un-ripened Pu'er tea).

Further, Pu'er tea contains a large amount of antioxidants which can scavenge free radicals after being absorbed by the organism, so as to prevent lipid peroxidation and improve hyperlipemia and hepatic steatosis.

Moreover, Pu'er tea has effects of decreasing blood lipids, improving insulin resistance and preventing cardiovascular diseases. In addition, Pu'er tea is effective to prevent atherosclerosis, cardiovascular diseases and cancer, and has effects of losing weight, lowering blood pressure, and opposing cancer. Research has proved that lovastatin exists in Pu'er tea. Lovastatin is known to competitively inhibit the HMG-CoA reductase in the synthesis of cholesterol, resulting in decreasing the synthesis speed of human cholesterol, so that the cholesterol can be regulated and the blood lipids can be decreased. The effect of ripened tea on decreasing blood lipids is much better than that of the un-ripened tea because the ripened tea can decrease the contents of both cholesterol and triglyceride. Further research shows that Pu'er ripened tea can mainly decrease the contents of low-density lipoprotein and triglyceride in plasma center.

The effects of Hunan dark tea are substantially same as that of Pu'er tea of Yunnan province because they both belong to post-fermented tea and have similar processing method. However, the present invention has found that the combined application of dried tangerine peels and Hunan dark tea has significant better effect than that of the combined application of dried tangerine peels and Ripened Pu'er tea with respect to decrease blood glucose, although the hypolipidemic effect of the former is slightly less than that of the latter. The reason may be associated with the Eurotiumcristatum in the dark tea in Hunan province. Experiments in vitrio indicate that the Eurotiumcristatum not only can dissolve the fat of the body, but also can regulate the metabolism of glucides.

The pharmacological experiments according to the present invention indicate that the Fu tea, Jinfu tea, Qianliang tea and Bailiang tea are effective to improve glycometabolism regarding to the following effects: decreasing the concentration of fasting blood glucose, improving the tolerance of glycogen in the body, improving the non-sensitivity of insulin and glucagon and promoting glucose transport and lipid metabolism in liver. These indexes conform to functional evaluation criteria of health food set by MOHC, which illustrates that the Fu tea, Jinfu tea, Qianliang tea and Bailiang tea can be used as therapeutic or adjuvant drugs for people suffering from hyperglycemia and hyperlipoidemia.

The drug experiments according to the present invention indicate that the more fully fermented and the longer time the tea is left for aging, the higher concentration of the active ingredients will be formed in the tea, resulting in the more effective. Therefore, the secondary fermentation dark tea which is most fully fermented and longest aged, is selected as the raw material in the present invention. The beneficial substances and probiotics are concentrated to a even higher level by repeated "micro fermentation" of aging.

After years of research and practical exploration, the present invention has created a method in which dried tangerine peels are added to dark tea during its preparation process and are fermented together with the dark tea. Specifically, the dried tangerine peels are added to the dark tea during the process of brick pressing, and are fermented with the dark tea during the secondary fermentation. Studies indicate that the brick of dark tea produces a large amount of probiotics, which are mainly the "golden flower" (Eurotiumcristatum), and the Eurotiumcristatum can generate biochemical compositions with more comprehensive properties and stronger function based on the metabolic substrate comprising tea and dried tangerine peels.

Research results suggest that differential chemical compounds are found by chromatography and nuclear magnetic resonance from the mixing raw materials of dried tangerine peels and dark tea by the special fermentation according to the present invention. The differential chemical compounds are flavonoids which are not existed in the mixing raw materials before the special fermentation. Specifically, the flavonoids are quercetin and kaempferol, respectively.

The present invention creates a method of "Yang pi", that is to preserve the dried tangerine peels by shuffling placement of them together with Yunnan Pu'er tea or Hunan dark tea in a porcelain jar to perform a trans-contamination, which leads to mutually absorb the beneficial substances and probiotic bacteria between the dried tangerine peels and Yunnan Pu'er tea or Hunan dark tea. The "Yang pi" method results in increasing types of probiotic bacteria and metabolic substances in the two materials, respectively, and enrichments of the quantities and concentrations of the beneficial substance in the two materials, respectively.

It is found in the present invention that the probiotic substances and/or their concentrations in the composition of tea and dried tangerine peels may differ when diverse tea or diverse dried tangerine peels are used, and even when the same tea or same dried tangerine peels but with different aging degrees are used. For the purpose of absorbing the beneficial substances of tea and dried tangerine peels into the traditional Chinese medicine composition provided by the present invention as much as possible, the present invention creates a method of multiply mixing the various raw materials according to different ratios.

For example, the wild tea tree leaves and human planting tea tree leaves are selected. Those tea leaves are aged for 1 year, 2 years, 3 years and 5 years, respectively. They are mixed together.

Different types of tea can be mixed together, for instance, mixing Jinfu tea with Qianliang tea or Bailiang tea, mixing Fu tea with Pu'er tea, or mixing Pu'er tea with Qianliang tea or Bailiang tea, mixing Fu tea with Qianliang tea or Bailiang tea, mixing Fu tea with Pu'er tea, or mixing Pu'er tea with Qianliang tea or Bailiang tea.

Different types of tangerine peels can be mixed together, for instance, mixing green tangerine peels with yellow-green tangerine peels, mixing green tangerine peels with yellow-red tangerine peels, mixing yellow-green tangerine peels with yellow-red tangerine peels, or mixing green tangerine peels with yellow-green tangerine peels, and yellow-red tangerine peels.

In terms of the aging time, the dried tangerine peels aged from 5 to 15 years or older than 15 years are mixed in different ratios.

Above mixture can strengthen synergistic pharmaceutical effects by aggregating or concentrating the specific substances in various teas and dried tangerine peels.

The composition of dried tangerine peels and dark tea of the present invention combines the pharmaceutical functions of the both materials. The dried tangerine peels can decrease blood glucose, and the dark tea has effects of regulating lipids, losing weight, decreasing blood pressure and regulating metabolism of glucoses.

The mixture is processed by the method of aging the tea leaves and dried tangerine peels, mixing different types of tea leaves with different aged period with different types of tangerine peels with different aged periods, adding the dried tangerine peels into the dark tea for joint post-fermentation and repeatedly performing micro fermentations. As a result, the traditional Chinese medicine composition of the present invention has special, clinical and comprehensive effects of regulating metabolism of glucoses, lipids, weight and blood pressure. It is effective to control the occurrence and development of the complications of diabetes from several aspects.

In a preferred embodiment of the present invention, the "Yang pi" process is to mix placement of the dried tangerine peels with the ripened Yunnan Pu'er tea in a porcelain jar, and age them for 2 to 3 years.

In a preferred embodiment of the present invention, the "Yang pi" process is to mix placement of the dried tangerine peels with the Yunnan Pu'er raw tea in a porcelain jar, and age them 5 years or more.

In a preferred embodiment of the present invention, the "Yang pi" process is to mix placement of the dried tangerine peels with the Hunan dark tea in a porcelain jar, and age them for 2 to 3 years.

In a preferred embodiment of the present invention, the composition of Yunnan ripened Pu'er tea and dried tangerine peels has prominent effects of decreasing blood lipids as well as blood glucose.

In another preferred embodiment of the present invention, the composition of Jinfu tea of Hunan Anhua county and dried tangerine peels has even more prominent effects of decreasing blood glucose.

The method for preparing a traditional Chinese medicine composition of dried tangerine peels and dark tea according to the present invention comprises steps of: adopting the different types of dried tangerine peels which are not preserved, mixing 3 parts (by weight) of dried tangerine peels and 1 part (by weight) of ripened Pu'er tea, and aging the mixture for 2 years or more, respectively for "Yang pi" porpurse; mixing the above-mentioned different types and differently aged preserved tangerine peels, and breaking the mixture of dried tangerine peels into small pieces; and adding the small pieces of dried tangerine peels into the black tea under the mixing ratio of 5 parts (by weight) to 15 parts (by weight) of the dried tangerine peels against 95 parts (by weight) to 85 parts (by weight) of black tea after pile fermentation; pressing the mixture into bricks, post-fermenting the bricks until the blossom of golden flower, and then aging the tea brick for about 2 years by first placing the tea bricks in a storehouse at temperatures slightly higher than the average room temperature for 0.5 year to 1 year, and then placing the tea bricks mixed with dried tangerine peels aged for 5 years or more into a porcelain jar, and further aging for 1 to 1.5 years, finally, the mixture can be used as the traditional Chinese medicine tea drinks for treating diabetes.

In another preferred embodiment of the present invention, the tea bricks after the above-mentioned about 2-year aging time are pulled apart and left in the air for about 30 days for oxidization. After the loosen tea leaves are oxidized for about 30 days, they are smashed into small particles or powders. And then another 5 parts (by weight) to 15 parts (by weight) of blended tangerine peels are taken and smashed into particles or powders. The above-mentioned tangerine peels, in particles or powders form, are blended into the above-mentioned black teas, in particles or powders form. Then the composition can be used as the traditional Chinese medical tea drinks for treating diabetes. General patients can drink the tea once or twice a day, each time 5-10 grams. Severe patients can drink twice a day, each time 10-20 grams.

In still another preferred embodiment of the present invention, 10 parts (by weight) of dried tangerine peels are added to the black tea for one-time during the brick pressing process.

In still another preferred embodiment of the present invention, the total amount of the dried tangerine peels is 20 parts (by weight). Among them, 10 parts (by weight) of dried tangerine peels are added to the black tea during the brick pressing process, the other 10 parts (by weight) of dried tangerine peels are added to the black tea after above-mentioned aging for 2 years.

EXAMPLE 1

The preparation method of the medicine composition of the present invention comprises steps of: selecting different types of mandarin oranges, preferably mandarin oranges from Xinhui county, Guangdong province, China, with green skin, yellow-green skin and yellow-red skin; drying the fruits in the natural conditions, when they lose 10-30% of juice, peeling the skins to obtain the peels of citrus fruits, aging the obtained peels of citrus fruits for 3 years to make them become the green tangerine peels, yellow-green tangerine peels and yellow-red tangerine peels, preserving (Yang Pi) the above-mentioned dried tangerine peels, respectively, by shuffling placement of the dried tangerine peels with ripened Pu'er tea in a porcelain jar under the mixing ratio of 3 parts (by weight) of dried tangerine peels and 1 part (by weight) of ripened Pu'er tea to perform trans-contamination for 2 to 3 years, after the trans-contamination, picking out the preserved tangerine peels from the ripened Pu'er tea, blending the preserved green tangerine peels, the yellow-green tangerine peels and the yellow-red tangerine peels in the ratio of 30 parts (by weight) of green tangerine peels, 35 parts (by weight) of yellow-green tangerine peels and 35 parts (by weight) of yellow-red tangerine peels, whose aged times vary from 5 to 15 years or even more than 15 years, wherein the dried tangerine peels of 5 to 6 years old accounts for 35% (by weight), the dried tangerine peels of 7 to 8 years old accounts for 25% (by weight), the dried tangerine peels of 9 to 10 years old accounts for 20% (by weight), the dried tangerine peels of 11 to 12 years old accounts for 12% (by weight), the dried tangerine peels of 13 to 14 years old accounts for 5% (by weight), and the dried tangerine peels of 15 years old or more than 15 years old accounts for 3% (by weight), breaking the blended dried tangerine peels into small chips for future use; selecting fresh tea leaves from the wild tea tree and fresh tea leaves from human planted tea tree, leaving and aging the tea leaves for about 3 years, then blending the aged wild tea leaves and the aged human planting tea leaves, pile-fermenting the blended wild tea leaves and human planting tea leaves to make them as black tea, after finishing the pile-fermentation, leaving and aging the black tea for 2 to 5 years, then adding 10 parts (by weight) of above-mentioned broken dried tangerine peels into the black tea, then pressing, in the presence of hot steam, the mixture into tea bricks, after making the tea bricks, conducting the secondary fermentation (post-fermentation), and again aging the tea bricks for about another 2 years. The obtained dark tea brick can be used as the medical composition to cure diabetes.

EXAMPLE 2

The preparation method of the medical composition of the present invention comprises steps of: selecting different types of mandarin oranges, preferably mandarin oranges from Xinhui county, Guangdong province China, with green skin, yellow-green skin and yellow-red skin; drying the fruits in the natural conditions, when they lose 10-30% of juice, peeling the skins to obtain the peels of citrus fruits, aging the obtained peels of citrus fruits for 3 years to make them become the green tangerine peels, yellow-green tangerine peels and yellow-red tangerine peels, preserving (Yang pi) the above-mentioned dried tangerine peels, respectively, by shuffling placement of the dried tangerine peels with ripened Pu'er tea in a porcelain jar under the mixing ratio of 3 parts (by weight) of dried tangerine peels and 1 part (by weight) of ripened Pu'er tea to perform trans-contamination for 2 to 3 years, after the trans-contamination, picking out the preserved tangerine peels from the ripened Pu'er tea, blending the preserved green tangerine peels, the yellow-green tangerine peels and the yellow-red tangerine peels in the ratio of 30 parts (by weight) of green tangerine peels, 35 parts (by weight) of yellow-green tangerine peels and 35 parts (by weight) of yellow-red tangerine peels, whose aged times vary from 5 to 15 years or even more than 15 years, wherein the dried tangerine peels of 5 to 6 years old accounts for 35% (by weight), the dried tangerine peels of 7 to 8 years old accounts for 25% (by weight), the dried tangerine peels of 9 to 10 years old accounts for 20% (by weight), the dried tangerine peels of 11 to 12 years old accounts for 12% (by weight), the dried tangerine peels of 13 to 14 years old accounts for 5% (by weight), and the dried tangerine peels of 15 years old or more than 15 years old accounts for 3% (by weight), breaking the blended dried tangerine peels into small chips for future use; selecting fresh tea leaves from the wild tea tree and fresh tea leaves from human planted tea tree, leaving and aging the tea leaves for about 3 years, then blending the aged wild tea leaves and the aged human planting tea leaves, pile-fermenting the blended wild tea leaves and human planting tea leaves to make them as black tea, after finishing the pile-fermentation, leaving and aging the black tea for 2 to 5 years, then adding 10 parts (by weight) of above-mentioned treated dried tangerine peels into the black tea, then pressing, in the presence of hot steam, the mixture into tea bricks, after making the tea bricks, conducting the secondary fermentation (post-fermentation), again aging the tea bricks for about another 2 years, pulling apart the tea bricks into loose tea leaves, exposing the loosed tea leaves in the air for about 30 days for oxidation, after the oxidation, breaking them into small chips or power, then adding another 10 parts (by weight) of the prepared particles or power of blended tangerine peels into the smashed tea particles or tea powder. And the obtained particled or powdered composition can be either directly used as medicine for treating diabetes, or used to further make tea bags for the convenience of taking along with.

EXAMPLE 3

The method for preparing the medicine composition comprising dried tangerine peels and Jinfu tea of the present invention comprises: preparation of dried tangerine peels, preparation of dark tea, blend of the dried tangerine peels and the dark tea, and age of the tea bricks comprising the dried tangerine peels and dark tea.

1. Preparation of Dried Tangerine Peels
(1) Citrus fruits are placed indoors for 3 days or more after being picked so as to let the water in the citrus fruits loose to about 10-30% by cool breeze and to let the fruit skin absorb, as much as possible, the fruit juice;
(2) The fleshes of citrus fruits are scooped out and the skins of citrus fruits are peeled off;
(3) The peels of citrus fruits are dried under the sun;
(4) The peels of citrus fruits need to be turned over at least once during the drying process and after the turn-over, continue to be dried for about 5 days until they are completely dried;
(5) The dried peels of citrus fruits are placed and stored in a place at a temperature slightly higher than the average room temperature, such as placing them on the top floor of a house;
(6) The newly dried peels of citrus fruits need to be covered with moisture-proof woolen blanket or other moisture-proof covers during humid climate;
(7) Dehumidifiers should be used to dehumidify when the humidity is very high;
(8) The peels of citrus fruits need to be dried under the sun again in the following summer time for 2 to 3 hours;
(9) After the secondary-time drying, the peels of citrus fruits are, again, put in a place with a temperature slightly higher than room temperature, such as the top floor of a house;
(10) The peels of citrus fruits after being dried for the secondary time are covered with moisture-proof woolen blanket or other moisture-proof covers during humid climate;
(11) The peels of citrus fruits are dried under the sun for 2 to 3 hours again (the third time of drying of peels of citrus fruits) in the summer of the third year;
(12) The peels of citrus fruits after being dried for 3 times can be stored in a place of an average room temperature, but should not be placed in a cool and high humidity room, such as a basement;
(13) The peels of citrus fruits are dried again in the sun for 2 to 3 hours in summer time of the fourth year;
(14) When the peels of citrus fruits are then stored to the autumn of the fourth year, they become dried tangerine peels, and the total aging time for the peels of citrus fruits should be 3 years or more;
(15) The dried tangerine peels are placed into a porcelain jar with Yunnan ripened Pu'er tea at the ratio of 3:1 (by weight), and are preserved (Yang pi) for 2 to 3 years, resulting in the fact that the dried tangerine peels can fully generate flavonoids and various beneficial substances after the mutual absorption and trans-contamination between them in the porcelain jar;
(16) After the above-mentioned preservation, the dried tangerine peels are picked out from the Yunnan ripened Pu'er tea;
(17) The preserved dried tangerine peels are further aged for some different years, to become dried tangerine peels of 5 years old to 15 years old or more than 15 years old.

After the above-mentioned preparation, the dried tangerine peels are ready to be used as the raw materials of the traditional Chinese medicine composition in the present invention.

2. Preprocessing of Dark Tea
(1) Collecting fresh tea leaves from the wild tea tree and fresh tea leaves from human planted tea tree in Anhua county, Hunan province of China, leaving and aging them for about 3 years, after the above-mentioned aging, pile-fermenting the wild tea leaves and human planting tea leaves, respectively, after finishing the pile-fermentation, again leaving and aging them for about 2 to 5 years;
(2) Blending the wild tea leaves and human planting tea leaves at the ratio of 1:9 (by weight);

(3) The mixture of the human planting tea leaves and wild tea leaves is further aged for 2 to 5 years for future use.

3. Mixing of the Dried Tangerine Peels and Black Tea (1) The dried tangerine peels of 5 to 15 years old are smashed into small chips for use;
(2) The flaked dried tangerine peels are mixed with the above-mentioned blended and 2 to 5 years aged black tea at the ratio of 1:9 (by weight) in dog days in summer, wherein the black tea aged for 2 years accounts for 40% (by weight), the black tea aged for 3 years accounts for 30% (by weight), the Black tea aging for 4 years accounts for 20% (by weight), and the black tea aged for 5 years accounts for 10% (by weight);
(3) The mixture is pressed into tea brick in the presence of steam;
(4) The pressed tea brick comprising dried tangerine peels and black tea undergoes secondary fermentation at the temperature of 28 to 30° C. and under the relative humidity of 60-70%; during the process of the secondary fermentation, the tea brick is moisturized every for 2 days until "golden flower" blooms, and becomes Jinfu tea.

4. Further Aging Process of the Tea Brick (1) The tea brick comprising dried tangerine peels and dark tea is aged in a storehouse with a temperature slightly higher than room temperature for half a year in order to let the tea brick further produce fermented substances after the secondary fermentation;
(2) Then the tea brick comprising dried tangerine peels and dark tea is placed into a porcelain jar with some dried tangerine peels of 5 years or more old at the mixing ratio of 8 to 2 (by weight), and the tea bricks are aged for 1.5 years so that the tea bricks can contact with the old tangerine peels to absorb beneficial substances and probiotic bacteria from the old tangerine peels.

Then the tea bricks can be either directly used as medical composition or further packaged as tea bags for diabetes patients to brew and drink.

EXAMPLE 4

The method for preparing the medical composition comprising dried tangerine peels and Jinfu tea of the present invention comprises: preparation of dried tangerine peels, preparation of dart tea, blend of the dried tangerine peels and the dark tea, age of the tea bricks comprising the dried tangerine peels and dark tea, and addition of 10 parts (by weight) of dried tangerine peels.

1. Preparation of Dried Tangerine Peels (1) Citrus fruits are placed indoors for 3 days or more after being picked so as to let the water in the citrus fruits loose to about 10-30% by cool breeze and to let the fruit skin absorb, as much as possible, the fruit juice;
(2) The fleshes of citrus fruits are scooped out and the skins of citrus fruits are peeled off;
(3) The peels of citrus fruits are dried under the sun;
(4) The peels of citrus fruits need to be turned over at least once during the drying process and after the turn-over, continue to be dried for about 5 days until they are completely dried;
(5) The dried peels of citrus fruits are placed and stored in a place at a temperature slightly higher than the average room temperature, such as placing them on the top floor of a house;
(6) The newly dried peels of citrus fruits need to be covered with moisture-proof woolen blanket or other moisture-proof covers in the humid climate;
(7) Dehumidifiers should be used to dehumidify when the humidity is very high;
(8) The peels of citrus fruits need to be dried again in the following summer time for 2 to 3 hours;
(9) After the secondary-time drying, the peels of citrus fruits are, again, put in a place with a temperature slightly higher than room temperature, such as the top floor of a house;
(10) The peels of citrus fruits after being dried for the secondary time are covered with moisture-proof woolen blanket or other moisture-proof covers in the humid climate;
(11) The peels of citrus fruits are dried under the sun for 2 to 3 hours again (the third time of drying of peels of citrus fruits) in the summer of the third year;
(12) The peels of citrus fruits after being dried for 3 times can be placed in a place of an average room temperature, but should not be placed in a cool and high humidity room, such as a basement;
(13) The peels of citrus fruits are dried again in the sun for 2 to 3 hours in summer time of the fourth year;
(14) When the peels of citrus fruits are then stored to the autumn of the fourth year, they become dried tangerine peels, and the total aging time for the peels of citrus fruits should be 3 years or more;
(15) The dried tangerine peels are placed into a porcelain jar with Yunnan ripened Pu'er tea at the ratio of 3:1 (by weight), and are preserved (Yang pi) for 2 to 3 years, resulting in the fact that the dried tangerine peels can fully generate flavonoids and various beneficial substances after the mutual absorption and trans-contamination between them in the porcelain jar;
(16) After the above-mentioned preservation, the dried tangerine peels are picked out from the Yunnan ripened Pu'er tea;
(17) The preserved dried tangerine peels are further aged for some different years, to become dried tangerine peels of 5 years old to 15 years old or more than 15 years old.

After the above-mentioned preparation, the dried tangerine peels are ready to be used as the raw materials of the traditional Chinese medicine composition in the present invention.

2. Preprocessing of Dark Tea (1) Collecting fresh tea leaves from the wild tea tree and fresh tea leaves from human planted tea tree in Anhua county, Hunan province of China, leaving and aging them for about 3 years, after the above-mentioned aging, pile-fermenting the wild tea leaves and human planting tea leaves, respectively, after finishing the pile-fermentation, again leaving and aging them for about 2 to 5 years;
(2) Blending the wild tea leaves and human planting tea leaves at the ratio of 1:9 (by weight);
(3) The mixture of the human planting tea leaves and wild tea leaves is further aged for 2 to 5 years for future use.

3. Mixing of the Dried Tangerine Peels and the Aged Tea Leaves (1) The dried tangerine peels of 5 to 15 years old are smashed into small chips for use;
(2) The flaked dried tangerine peels are mixed with the above-mentioned blended and 2 to 5 years aged tea leaves at the ratio of 1 to 9 (by weight) in dog days in summer, wherein the black tea aged for 2 years accounts for 40% (by weight), the black tea aged for 3 years accounts for 30% (by weight), the black tea aging for 4 years accounts for 20% (by weight), and the black tea aged for 5 years accounts for 10% (by weight);
(3) The mixture is pressed into tea brick in the presence of steam;

(4) The pressed tea brick comprising dried tangerine peels and black tea undergoes secondary fermentation at the temperature of 28 to 30° C. and under the relative humidity of 60-70%; during the process of the secondary fermentation, the tea brick is moisturized every for 2 days until "golden flower" blooms, and becomes Jinfu tea.

4. Further Aging Process of the Tea Brick (1) The tea brick comprising dried tangerine peels and dark tea is aged in a storehouse with a temperature slightly higher than room temperature for half a year in order to let the tea brick further produce fermented substances after the secondary fermentation;
(2) Then the tea brick comprising dried tangerine peels and dark tea is placed into a porcelain jar with some dried tangerine peels of 5 years or more old at the mixing ratio of 8 to 2 (by weight), and the tea bricks are aged for 1.5 years so that the tea bricks can contact with the old tangerine peels to absorb beneficial substances and probiotic bacteria from the old tangerine peels.

5. Addition of Dried Tangerine Peels (1) The 2-year aged tea brick comprising dried tangerine peels and dark tea is pulled apart;
(2) The loosed tea leaves are left in the air and oxidized naturally for 30 days at the room temperature;
(3) 10 parts (by weight) of dried tangerine peels of more than 10 years are smashed into particles or powder; and
(4) The dried tangerine peels smashed into particles or powder are mixed with the loose tea leaves.

Then the mixture can be either directly used as medical composition or further packaged as tea bags for diabetes patients to brew and drink.

EXAMPLE 5

The method for preparing the medical composition comprising dried tangerine peels and Qiangliang tea or Bailiang tea of the present invention comprises: preparation of dried tangerine peels, preparation of dart tea, blend of the dried tangerine peels and the black tea, and age of the tea bricks comprising the dried tangerine peels and dark tea.

1. Preparation of Dried Tangerine Peels (1) Citrus fruits are placed indoors for 3 days or more after being picked so as to let the water in the citrus fruits loose to about 10-30% by cool breeze and to let the fruit skin absorb, as much as possible, the fruit juice;
(2) The fleshes of citrus fruits are scooped out and the skins of citrus fruits are peeled off;
(3) The peels of citrus fruits are dried under the sun;
(4) The peels of citrus fruits need to be turned over at least once during the drying process and after the turn-over, continue to be dried for about 5 days until they are completely dried;
(5) The dried peels of citrus fruits are placed and stored in a place at a temperature slightly higher than the average room temperature, such as placing them on the top floor of a house;
(6) The newly dried peels of citrus fruits need to be covered with moisture-proof woolen blanket or other moisture-proof covers in the humid climate;
(7) Dehumidifiers should be used to dehumidify when the humidity is very high;
(8) The peels of citrus fruits need to be dried again in the following summer time for 2 to 3 hours;
(9) After the secondary-time drying, the peels of citrus fruits are, again, put in a place with a temperature slightly higher than room temperature, such as the top floor of a house;
(10) The peels of citrus fruits after being dried for the secondary time are covered with moisture-proof woolen blanket or other moisture-proof covers in the humid climate;
(11) The peels of citrus fruits are dried under the sun for 2 to 3 hours again (the third time of drying of peels of citrus fruits) in the summer of the third year;
(12) The peels of citrus fruits after being dried for 3 times can be placed in a place of an average room temperature, but should not be placed in a cool and high humidity room, such as a basement;
(13) The peels of citrus fruits are dried again in the sun for 2 to 3 hours in summer time of the fourth year;
(14) When the peels of citrus fruits are then stored to the autumn of the fourth year, they become dried tangerine peels, and the total aging time for the peels of citrus fruits should be 3 years or more;
(15) The dried tangerine peels are placed into a porcelain jar with Yunnan ripened Pu'er tea at the ratio of 3:1 (by weight), and are preserved (Yang pi) for 2 to 3 years, resulting in the fact that the dried tangerine peels can fully generate flavonoids and various beneficial substances after the mutual absorption and trans-contamination between them in the porcelain jar;
(16) After the above-mentioned preservation, the dried tangerine peels are picked out from the Yunnan ripened Pu'er tea;
(17) The preserved dried tangerine peels are further aged for some different years, to become dried tangerine peels of 5 years old to 15 years old or more than 15 years old.

After the above-mentioned preparation, the dried tangerine peels are ready to be used as the raw materials of the traditional Chinese medicine composition in the present invention.

2. Preprocessing of Dark Tea (1) Collecting fresh tea leaves from the wild tea tree and fresh tea leaves from human planted tea tree in Anhua county, Hunan province of China, leaving and aging them for about 3 years, after the above-mentioned aging, pile-fermenting the wild tea leaves and human planting tea leaves, respectively, after finishing the pile-fermentation, again leaving and aging them for about 2 to 5 years;
(2) Blending the wild tea leaves and human planting tea leaves at the ratio of 1:9 (by weight);
(3) The mixture of the human planting tea leaves and wild tea leaves is further aged for 2 to 5 years for future use.

3. Mixing of the Dried Tangerine Peels and Black Tea (1) The dried tangerine peels of 5 to 15 years old are smashed into small chips for use;
(2) The flaked dried tangerine peels are mixed with the above-mentioned blended and 2 to 5 years aged black tea at the ratio of 1 to 9 (by weight) in Spring and Autumn, wherein the black tea aged for 2 years accounts for 40% (by weight), the black tea aged for 3 years accounts for 30% (by weight), the black tea aging for 4 years accounts for 20% (by weight), and the black tea aged for 5 years accounts for 10% (by weight);
(3) The mixture is pressed into tea columns in the presence of steam, and the tea columns are wrapped up with dried reed leaves;
(4) The pressed and wrapped tea columns undergoes secondary fermentation in open air in Spring and Autumn time for about 50 days until the tea columns bloom "golden flower".

4. Further Aging Process of the Tea Columns (1) The tea columns comprising dried tangerine peels and dark tea are aged in a storehouse with a temperature slightly higher than room temperature for half a year in order to let the tea brick further produce fermented substances after the secondary fermentation;
(2) Then the tea columns comprising dried tangerine peels and dark tea are placed into porcelain jars with some dried tangerine peels of 5 or more years old at the mixing ratio of 8 to 2 (by weight), and the tea columns are aged for 1.5 years so that the tea columns can contact with the old tangerine peels to absorb beneficial substances and probiotic bacteria from the old tangerine peels.

Then the tea columns can be either directly used as medical composition or further packaged as tea bags for diabetes patients to brew and drink.

EXAMPLE 6

The method for preparing the medical composition comprising dried tangerine peels and Qiangliang tea or Bailiang tea of the present invention comprises: preparation of dried tangerine peels, preparation of dart tea, blend of the dried tangerine peels and the black tea, age of the tea bricks comprising the dried tangerine peels and dark tea, and addition of 10 parts (by weight) of dried tangerine peels.

1. Preparation of Dried Tangerine Peels
(1) Citrus fruits are placed indoors for 3 days or more after being picked so as to let the water in the citrus fruits loose to about 10-30% by cool breeze and to let the fruit skin absorb, as much as possible, the fruit juice;
(2) The fleshes of citrus fruits are scooped out and the skins of citrus fruits are peeled off;
(3) The peels of citrus fruits are dried under the sun;
(4) The peels of citrus fruits need to be turned over at least once during the drying process and after the turn-over, continue to be dried for about 5 days until they are completely dried;
(5) The dried peels of citrus fruits are placed and stored in a place at a temperature slightly higher than the average room temperature, such as placing them on the top floor of a house;
(6) The newly dried peels of citrus fruits need to be covered with moisture-proof woolen blanket or other moisture-proof covers in the humid climate;
(7) Dehumidifiers should be used to dehumidify when the humidity is very high;
(8) The peels of citrus fruits need to be dried again in the following summer time for 2 to 3 hours;
(9) After the secondary-time drying, the peels of citrus fruits are, again, put in a place with a temperature slightly higher than room temperature, such as the top floor of a house;
(10) The peels of citrus fruits after being dried for the secondary time are covered with moisture-proof woolen blanket or other moisture-proof covers in the humid climate;
(11) The peels of citrus fruits are dried under the sun for 2 to 3 hours again (the third time of drying of peels of citrus fruits) in the summer of the third year;
(12) The peels of citrus fruits after being dried for 3 times can be placed in a place of an average room temperature, but should not be placed in a cool and high humidity room, such as a basement;
(13) The peels of citrus fruits are dried again in the sun for 2 to 3 hours in summer time of the fourth year;
(14) When the peels of citrus fruits are then stored to the autumn of the fourth year, they become dried tangerine peels, and the total aging time for the peels of citrus fruits should be 3 years or more;
(15) The dried tangerine peels are placed into a porcelain jar with Yunnan ripened Pu'er tea at the ratio of 3:1 (by weight), and are preserved (Yang pi) for 2 to 3 years, resulting in the fact that the dried tangerine peels can fully generate flavonoids and various beneficial substances after the mutual absorption and trans-contamination between them in the porcelain jar;
(16) After the above-mentioned preservation, the dried tangerine peels are picked out from the Yunnan ripened Pu'er tea;
(17) The preserved dried tangerine peels are further aged for some different years, to become dried tangerine peels of 5 years old to 15 years old or more than 15 years old.

After the above-mentioned preparation, the dried tangerine peels are ready to be used as the raw materials of the traditional Chinese medicine composition in the present invention.

2. Preprocessing of Dark Tea
(1) Collecting fresh tea leaves from the wild tea tree and fresh tea leaves from human planted tea tree in Anhua county, Hunan province of China, leaving and aging them for about 3 years, after the above-mentioned aging, pile-fermenting the wild tea leaves and human planting tea leaves, respectively, after finishing the pile-fermentation, again leaving and aging them for about 2 to 5 years;
(2) Blending the wild tea leaves and human planting tea leaves at the ratio of 1:9 (by weight);
(3) The mixture of the human planting tea leaves and wild tea leaves is further aged for 2 to 5 years for future use.

3. Mixing of the Dried Tangerine Peels and the Black Tea Leaves
(1) The dried tangerine peels of 5 to 15 years old are smashed into small chips for use;
(2) The flaked dried tangerine peels are mixed with the above-mentioned blended and 2 to 5 years aged black tea at the ratio of 1 to 9 (by weight) in Spring and Autumn, wherein the black tea aged for 2 years accounts for 40% (by weight), the black tea aged for 3 years accounts for 30% (by weight), the black tea aging for 4 years accounts for 20% (by weight), and the black tea aged for 5 years accounts for 10% (by weight);
(3) The mixture is pressed into tea columns in the presence of steam, and the tea columns are wrapped up with dried reed leaves;
(4) The pressed and wrapped tea columns undergoes secondary fermentation in open air in Spring and Autumn time for about 50 days until the tea columns bloom "golden flower".

4. Further Aging Process of the Tea Columns
(1) The tea columns comprising dried tangerine peels and dark tea are aged in a storehouse with a temperature slightly higher than room temperature for half a year in order to let the tea brick further produce fermented substances after the secondary fermentation;
(2) Then the tea columns comprising dried tangerine peels and dark tea are placed into porcelain jars with some dried tangerine peels of 5 or more years old at the mixing ratio of 8 to 2 (by weight), and the tea columns are aged for 1.5 years so that the tea columns can contact with the old tangerine peels to absorb beneficial substances and probiotic bacteria from the old tangerine peels.

5. Addition of Dried Tangerine Peels
(1) The 2-year aged tea columns comprising dried tangerine peels and dark tea are pulled apart;
(2) The loosed tea leaves are left in the air and oxidized naturally for 30 days at room temperature;
(3) 10 parts (by weight) of dried tangerine peels of more than 10 years old are smashed into particles or powder; and (4) The dried tangerine peels smashed into particles or powder are mixed with the loose tea leaves.

Then the mixture can be either directly used as medical composition or further packaged as tea bags for diabetes patients to brew and drink.

Clinical Experiment Examples

Case 1

Patient: male, 43 years old,

Oct. 23, 2016: fasting blood glucose was 8.9 mml. The patient administrated metformin, three times a day, one tablet each time before meals.

Oct. 24, 2016: the value of fasting blood glucose was 7.5 mml, with administration of metformin.

Oct. 25, 2016: the value of fasting blood glucose was 7.4 mml, with administration of metformin.

Oct. 26, 2016: the value of fasting blood glucose was 8.3 mml, with administration of metformin. The patient had a big dinner and drunk wine in the evening of October 25.

Oct. 27 to Oct. 28, 2016: the test of blood glucose was not performed, and the metformin was administrated as usual.

Oct. 29, 2016: the value of fasting blood glucose was 6.8 mml, and the traditional Chinese medicine tea drinks of the present invention were administrated twice a day, each time 5 grams of the tea, with the continuation of administration of the metformin.

Oct. 30, 2016: the value of fasting blood glucose was 6.2 mml, and the traditional Chinese medicine tea drinks of the present invention was continued to be administrated together with the administration of the metformin.

Oct. 31 to Nov. 4, 2016: the test of blood glucose was not performed, and the traditional Chinese medicine tea drinks of the present invention was continued to be administrated together with the administration of chemical medicine.

Nov. 5, 2016: the value of fasting blood glucose was 5.5 mml, and the tea drinks of the present invention were administrated without administrating the traditional Chinese medicine tea drinks of the present invention.

Nov. 6 to Nov. 12, 2016: the test of blood glucose was not performed, and the traditional Chinese medicine tea drinks of the present invention was continued to be administrated together with the administration of chemical medicine.

Nov. 13, 2016: the value of fasting blood glucose measured by a blood glucose meter was 6.5 mml, and the traditional Chinese medicine tea drinks of the present invention were administrated together with the administration of chemical medicine.

Nov. 14 to Nov. 19, 2016: the test of blood glucose was not performed, and the traditional Chinese medicine tea drinks of the present invention was continued to be administrated without the administration of chemical medicine.

Nov. 20, 2016: the value of fasting blood glucose was 6.3 mml, and the traditional Chinese medicine tea drinks of the present invention were administrated without administrating chemical medicine.

Nov. 21, 2016: the test of blood glucose was not performed, and the traditional Chinese medicine tea drinks of the present invention were administrated without administrating chemical medicine.

Nov. 22, 2016: the value of fasting blood glucose was 6.6 mml, and the traditional Chinese medicine tea drinks of the present invention were administrated without administrating chemical medicine.

Nov. 23 to Nov. 25, 2016: the test of blood glucose was not performed from, and the traditional Chinese medicine tea drinks of the present invention were administrated without administrating chemical medicine.

Nov. 26, 2016: the value of fasting blood glucose measured by a blood glucose meter was 7.1 mml, and the traditional Chinese medicine tea drinks of the present invention were administrated without administrating chemical medicine.

Nov. 27, 2016: the value of fasting blood glucose measured by a blood glucose meter was 7.0 mml, and the traditional Chinese medicine tea drinks of the present invention were administrated without administrating chemical medicine.

Nov. 28, 2016: the value of fasting blood glucose measured by a blood glucose meter was 6.3 mml, and the traditional Chinese medicine tea drinks of the present invention were administrated without administrating chemical medicine.

Nov. 29, 2016: the value of fasting blood glucose measured by a blood glucose meter was 6.3 mml, and the traditional Chinese medicine tea drinks of the present invention were administrated without administrating chemical medicine.

Nov. 30 to Dec. 25, 2016: the test of blood glucose was not performed, and the traditional Chinese medicine tea drinks of the present invention were administrated without administrating chemical medicine during that period.

Dec. 3, 2016: the value of fasting blood glucose was 5.3 mml, and the traditional Chinese medicine tea drinks of the present invention were administrated without administrating chemical medicine. On the previous day, the patient only ate little starch food but vegetables for the supper in the evening.

From the above-mentioned examples, it was found that the measured average value of blood glucose was 7.5 mml with the administration of metformin during 9 days from October 20 to October 29.

The measured average value of blood glucose was 6.1 mml with the joint administration of metformin and the traditional Chinese medicine tea drinks of the present invention during 22 days from October 29 to November 19.

The measured average value of blood glucose was 6.4 mml with only the administration of the traditional Chinese medicine tea drinks during 14 days from November 20 to December 13. The blood glucose value increased from 6.3 mml to the highest 7.1 mml in the first few days, and then decreased to about 6 mml a week later. It suggested only used the tea drinks of the present invention is similar to, if not better, the effect of the joint administration of metformin and the traditional Chinese medicine tea drinks of the present invention. The lowest value of 5.3 mml was observed in the experiment during the period when the tea drinks of the present invention were only used.

The metformin acts on gastrointestinal tract, and is essentially lack of long-lasting blood glucose decreasing effect because the glucose absorption to intestinal tract can be reduced by administration with meals. The patient of the above-mentioned case was not administrated with metformin from November 20 to December 3, totally 2 weeks, and the test results should not be interfered by the lasting effects of metformin during that period.

Case 2

Subject: The patient is a 52-year-old male, who has a long history of diabetes. Before drinking the traditional Chinese medicine tea drinks of the present invention, the subject administrated hypoglycemic agents (metformin) for long before each meal, each time 2 tablets.

Test results (measured on empty stomach at 7 o'clock in the morning)

| (Administration of metformin, only) | |
|---|---|
| Aug. 24, 2016: | 9.4 mml |
| Aug. 28, 2016: | 9.9 mml |
| Sep. 3, 2016: | 12.5 mml |
| Sep. 11, 2016: | 8.7 mml |
| Sep. 23, 2016: | 11.6 mml |
| Oct. 1, 2016: | 11 mml |
| Oct. 4, 2016: | 12.7 mml |
| Oct. 11, 2016: | 15.9 mml |
| Oct. 24, 2016: | 19.5 mml |
| Nov. 1, 2016: | 14.5 mml |
| Nov. 5, 2016: | 13.4 mml |
| Nov. 10, 2016: | 11.1 mml |
| Nov. 13, 2016: | 13 mml |
| Nov. 18, 2016: | 14 mml |
| Nov. 20, 2016: | 8.5 mml |
| Nov. 27, 2016: | 9.4 mml |
| Dec. 2, 2016: | 11.8 mml |
| Dec. 9, 2016: | 12.6 mml |
| Dec. 14, 2016: | 11.9 mml |
| Dec. 18, 2016: | 12.3 mml |
| Dec. 24, 2016: | 12.5 mml |
| Dec. 28, 2016: | 14.7 mml |
| Jan. 2, 2017: | 13.3 mml |
| Jan. 6, 2017: | 11.8 mml |
| (Administration of the tea drinks, only) | |
| Jan. 10, 2017: | 9 mml |
| Jan. 14, 2017: | 7 mml |
| Jan. 17, 2017: | 7.6 mml |
| Jan. 22, 2017: | 8.5 mml |
| Jan. 27, 2017: | 8 mml |
| Feb. 1, 2017: | 7.6 mml |
| Feb. 4, 2017: | 11.1 mml |
| Feb. 6, 2017: | 8.3 mml |
| Feb. 10, 2017: | 8.9 mml |
| Feb. 18, 2017: | 8.7 mml |
| Feb. 21, 2017: | 10.6 mml |
| Feb. 25, 2017: | 9.1 mml |
| Feb. 28, 2017: | 8.4 mml |
| Mar. 1, 2017: | 8.1 mml |
| Mar. 5, 2017: | 8.3 mml |

From the above case, it can be seen that only administration of metformin to decrease blood glucose would not lead to a good controlling effect, and the average value of blood glucose was 12.3 mml with a large fluctuation that varies from the 8.5 mml to the highest 19.5 mml After drinking the traditional Chinese medicine tea drinks of the present invention (brewing 1 to 2 bags every day), the average value of blood glucose was 8.6 mml with a steady trend where the values were fluctuated within 7-10 mml without the occurrence of very high measured results.

The two cases show that the traditional Chinese medicine tea drinks of the present invention have significant curing effects on diabetes.

Case 3

Patient: 39-year-old, female

The tested fasting blood glucose value was 17.5 mml before drinking the traditional Chinese medicine tea drinks of the present invention, and became 7.2 mml after 2-week drinking of the tea drinks. During that period, in the first week, the subcutaneous injections of 8 u of insulin were performed before breakfast and supper, and were stopped in the secondary week.

Case 4

Patient: 65-year-old, female

The tested fasting blood glucose value was 11.2 mml before drinking the traditional Chinese medicine tea drinks of the present invention, and became 6.8 mml after 2-week drinking of the tea drinks. During that period, in the first week, 0.5 mg of metformin was administrated before each meal and was stopped in the secondary week.

Case 5

Patient: 53-year-old, male

The tested fasting blood glucose value was 15 mml before drinking the traditional Chinese medicine tea drinks of the present invention, and became 7.5 mml after 2-week drinking of the tea drinks. During that period, in the first week, 50 mg of acarbose was administrated with the first mouthful food and was stopped in the secondary week.

Case 6

Patient: 67-year-old, female

The tested fasting blood glucose value was 12 mml before drinking the traditional Chinese medicine tea drinks of the present invention, and became 5.4 mml after 2-week drinking of the tea drinks. During that period, in the first week, the subcutaneous injections of 10 u of insulin were performed before meals and were stopped in the secondary week.

Case 7

Patient: 70-year-old, female

The tested fasting blood glucose value was 9 mml before drinking the traditional Chinese medicine tea drinks of the present invention, and became 5.8 mml after 2 week drinking of the tea drinks. During that period, in the first week, 80 mg of gliclazide was administrated and was stopped in the secondary week.

Case 8

Patient: 79-year-old, female

The tested fasting blood glucose value was 12.1 mml before drinking the traditional Chinese medicine tea drinks of the present invention, and became 7.6 mml after 2 week drinking of the tea drinks. During that period, in the first week, 50 mg of acarbose was administrated with the first mouthful food and was stopped in the secondary week.

Case 9

Patient: 74-year-old, male

The tested fasting blood glucose value was 8.4 mml before drinking the traditional Chinese medicine tea drinks of the present invention, and became 7.9 mml after 2 week drinking of the tea drinks. During that period, in the first week, 80 mg of gliclazide was administrated and was stopped in the secondary week.

Case 10

Patient: 67-year-old, male

The tested fasting blood glucose value was 8.2 mml before drinking the traditional Chinese medicine tea drinks of the present invention, and became 7.8 mml after 2 week drinking of the tea drinks. During the meantime, diamicron was administrated.

Case 11

Patient: 75-year-old, male

The tested fasting blood glucose value was 11.9 mml before drinking the traditional Chinese medicine tea drinks of the present invention, and became 9.1 mml after 2-week drinking of the tea drinks. During that period, in the first week, the subcutaneous injections of insulin were performed before breakfasts and suppers and were stopped in the secondary week.

Case 12

Patient: 62-year-old, female

The tested fasting blood glucose value was 14.8 mml before drinking the traditional Chinese medicine tea drinks of the present invention, and became 8.9 mml after 2-week drinking of the tea drinks. During that period, in the first week, the subcutaneous injections of insulin were performed before breakfasts and suppers and were stopped in the secondary week.

Case 13
Patient: 68-year-old, female
The tested fasting blood glucose value was 10.6 mml before drinking the traditional Chinese medicine tea drinks of the present invention, and became 7.1 mml after 2 week drinking of the tea drinks. During that period, in the first week, 50 mg of acarbose and pioglitazone was administrated with the first mouthful food and was stopped in the secondary week.

Case 14
Patient: 60-year-old, male
The tested fasting blood glucose value was 9.4 mml before drinking the traditional Chinese medicine tea drinks of the present invention, and became 7.9 mml after 2-week drinking of the tea drinks. During that period, in the first week, the subcutaneous injections of insulin were performed before breakfasts and suppers and were stopped in the secondary week.

Case 15
Patient: 56-year-old, female
The tested fasting blood glucose value was 9.1 mml before drinking the traditional Chinese medicine tea drinks of the present invention, and became 6.9 mml after 2-week drinking of the tea drinks. During that period, in the first week, 50 mg of acarbose and pioglitazone was administrated with the first mouthful food and was stopped in the secondary week.

Case 16
Patient: 49-year-old, female
The tested fasting blood glucose value was 8.8 mml before drinking the traditional Chinese medicine tea drinks of the present invention, and became 6.9 mml after 2-week drinking of the tea drinks. During that period, in the first week, 80 mg of gliclazide was administrated and was stopped in the secondary week.

Case 17
Patient: 63-year-old, male
The tested fasting blood glucose value was 11.4 mml before drinking the traditional Chinese medicine tea drinks of the present invention, and became 8.1 mml after 2-week drinking of the tea drinks. During that period, in the first week, the subcutaneous injections of insulin were performed before breakfasts and suppers and were stopped in the secondary week.

Case 18
Patient: 59-year-old, male
The tested fasting blood glucose value was 9.7 mml before drinking the traditional Chinese medicine tea drinks of the present invention, and became 6.5 mml after 2-week drinking of the tea drinks. During that period, in the first week, the subcutaneous injections of insulin were performed before breakfasts and suppers and were stopped in the secondary week.

Case 19
Patient: 61-year-old, male
The tested fasting blood glucose value was 8.0 mml before drinking the traditional Chinese medicine tea drinks of the present invention, and became 5.9 mml after 2 week drinking of the tea drinks. During that period, in the first week, 50 mg of acarbose and pioglitazone was administrated with the first mouthful food and was stopped in the secondary week.

Case 20
Patient: 68-year-old, male
The tested fasting blood glucose value was 17.5 mml before drinking the traditional Chinese medicine tea drinks of the present invention, and became 7.2 mml after 2-week drinking of the tea drinks. During that period, in the first week, the subcutaneous injections of 8 u of insulin were performed before meals and were stopped in the secondary week.

Case 21
Patient: 46-year-old, male
The tested fasting blood glucose value was 15.1 mml before drinking the traditional Chinese medicine tea drinks of the present invention, and became 10.0 mml after 2-week drinking of the tea drinks. During that period, in the first week, chemical medicine was administrated and was stopped in the secondary week.

Case 22
Patient: 53-year-old, male
The tested fasting blood glucose value was 7.8 mml before drinking the traditional Chinese medicine tea drinks of the present invention, and became 6.3 mml after 2 week drinking of the tea drinks. During that period, in the first week, 50 mg of acarbose and pioglitazone was administrated with the first mouthful food and was stopped in the secondary week.

Case 23
Patient: 62-year-old, female
The tested fasting blood glucose value was 6.9 mml before drinking the traditional Chinese medicine tea drinks of the present invention, and became 5.8 mml after 2 week drinking of the tea drinks. During that period, in the first week, 50 mg of acarbose was administrated with the first mouthful food and was stopped in the secondary week.

Case 24
Patient: 71-year-old, male
The tested fasting blood glucose value was 9.6 mml before drinking the traditional Chinese medicine tea drinks of the present invention, and became 6.9 mml after 2 week drinking of the tea drinks. During that period, in the first week, 80 mg of gliclazide was administrated with the first mouthful food and was stopped in the secondary week.

Case 25
Patient: 48-year-old, female
The tested fasting blood glucose value was 8.1 mml before drinking the traditional Chinese medicine tea drinks of the present invention, and became 6.8 mml after 2-week drinking of the tea drinks. During that period, in the first week, the subcutaneous injections of insulin were performed before breakfasts and were stopped in the secondary week.

Case 26
Patient: 70-year-old, male
The tested fasting blood glucose value was 11.1 mml before drinking the traditional Chinese medicine tea drinks of the present invention, and became 9.3 mml after 2-week drinking of the tea drinks. During that period, in the first week, the subcutaneous injections of 8 units of insulin were performed before meals and stopped in the secondary week.

Case 27
Patient: 62-year-old, female
The tested fasting blood glucose value was 7.6 mml before drinking the traditional Chinese medicine tea drinks of the present invention, and became 6.5 mml after 2 week drinking of the tea drinks. During that period, in the first week, 50 mg of acarbose and pioglitazone was administrated with the first mouthful food and was stopped in the secondary week.

Case 28
    Patient: 66-year-old, male
    The tested fasting blood glucose value was 6.9 mml before drinking the traditional Chinese medicine tea drinks of the present invention, and became 5.7 mml after 2 week drinking of the tea drinks. During that period, in the first week, 80 mg of gliclazide was administered and was stopped in the secondary week.
Case 29
    Patient: 41-year-old, male
    The tested fasting blood glucose value was 10.8 mml before drinking the traditional Chinese medicine tea drinks of the present invention, and became 8.2 mml after 2 week drinking of the tea drinks. During that period, in the first week, 80 mg of gliclazide was administered and was stopped in the secondary week.
Case 30
    Patient: 60-year-old, male
    The tested fasting blood glucose value was 14.7 mml before drinking the traditional Chinese medicine tea drinks of the present invention, and became 8.8 mml after 2 week drinking of the tea drinks. During that period, in the first week, 50 mg of acarbose and pioglitazone was administrated with the first mouthful food and was stopped in the secondary week.
Case 31
    Patient: 58-year-old, male
    The tested fasting blood glucose value was 11.7 mml before drinking the traditional Chinese medicine tea drinks of the present invention, and became 10.5 mml after 2-week drinking of the tea drinks. During that period, in the first week, the subcutaneous injections of 8 units of insulin were performed before breakfasts and suppers and stopped in the secondary week.
Case 32
    Patient: 47-year-old, female
    The tested fasting blood glucose value was 8.1 mml before drinking the traditional Chinese medicine tea drinks of the present invention, and became 6.3 mml after 2 week drinking of the tea drinks. During that period, in the first week, 50 mg of acarbose and pioglitazone was administrated with the first mouthful food and was stopped in the secondary week.
Case 33
    Patient: 47-year-old, female
    The tested fasting blood glucose value was 7.6 mml before drinking the traditional Chinese medicine tea drinks of the present invention, and became 5.9 mml after 2 week drinking of the tea drinks. During that period, in the first week, 50 mg of acarbose was administrated with the first mouthful food and was stopped in the secondary week
Case 34
    Patient: 60-year-old, male
    The tested fasting blood glucose value was 8.1 mml before drinking the traditional Chinese medicine tea drinks of the present invention, and became 6.7 mml after 2 week drinking of the tea drinks. During that period, in the first week, 50 mg of 5 mg of glipizide and pioglitazone was administrated and was stopped in the secondary week
Case 35
    Patient: 52-year-old, male
    The tested fasting blood glucose value was 12.7 mml before drinking the traditional Chinese medicine tea drinks of the present invention, and became 9.4 mml after 2 week drinking of the tea drinks. During that period, in the first week, 50 mg of acarbose and pioglitazone was administrated with the first mouthful food and was stopped in the secondary week.
Case 36
    Patient: 54-year-old, female
    The tested fasting blood glucose value was 10.5 mml before drinking the traditional Chinese medicine tea drinks of the present invention, and became 8.6 mml after 2 week drinking of the tea drinks. During that period, in the first week, 2 mg of glimepiride was administered and was stopped in the secondary week.
Case 37
    Patient: 57-year-old, male
    The tested fasting blood glucose value was 8.9 mml before drinking the traditional Chinese medicine tea drinks of the present invention, and became 7.1 mml after 2 week drinking of the tea drinks. During that period, in the first week, 50 mg of acarbose and pioglitazone was administrated with the first mouthful food and was stopped in the secondary week.
Case 38
    Patient: 64-year-old, male
    The tested fasting blood glucose value was 6.9 mml before drinking the traditional Chinese medicine tea drinks of the present invention, and became 5.7 mml after 2 week drinking of the tea drinks. During that period, in the first week, 50 mg of acarbose and pioglitazone was administrated with the first mouthful food and was stopped in the secondary week.
Case 39
    Patient: 67-year-old, male
    The tested fasting blood glucose value was 8.5 mml before drinking the traditional Chinese medicine tea drinks of the present invention, and became 7.1 mml after 2-week drinking of the tea drinks. During that period, in the first week, the subcutaneous injections of 10 units of insulin were performed before breakfasts and suppers and stopped in the secondary week.
Case 40
    Patient: 56-year-old, female
    The tested fasting blood glucose value was 11.6 mml before drinking the traditional Chinese medicine tea drinks of the present invention, and became 7.9 mml after 2 week drinking of the tea drinks. During that period, in the first week, chemical medicine was administrated and was stopped in the secondary week.
Case 41
    Patient: 58-year-old, male
    The tested fasting blood glucose value was 8.6 mml before drinking the traditional Chinese medicine tea drinks of the present invention, and became 6.0 mml after 2 week drinking of the tea drinks. During that period, in the first week, 50 mg of acarbose and pioglitazone was administrated with the first mouthful food and was stopped in the secondary week.
Case 42
    Patient: 58-year-old, female
    The tested fasting blood glucose value was 8.9 mml before drinking the traditional Chinese medicine tea drinks of the present invention, and became 5.3 mml after 2 week drinking of the tea drinks. During that period, in the first week, 50 mg of acarbose and pioglitazone was administrated with the first mouthful food and was stopped in the secondary week.

Case 43
 Patient: 70-year-old, male
 The tested fasting blood glucose value was 13.3 mml before drinking the traditional Chinese medicine tea drinks of the present invention, and became 10.5 mml after 2-week drinking of the tea drinks. During that period, in the first week, the subcutaneous injections of 8 units of insulin were performed before meals and stopped in the secondary week.

Case 44
 Patient: 61-year-old, male
 The tested fasting blood glucose value was 15.6 mml before drinking the traditional Chinese medicine tea drinks of the present invention, and became 9.7 mml after 2 week drinking of the tea drinks. During that period, in the first week, 50 mg of acarbose and pioglitazone was administrated with the first mouthful food and was stopped in the secondary week.

Case 45
 Patient: 65-year-old, male
 The tested fasting blood glucose value was 9.5 mml before drinking the traditional Chinese medicine tea drinks of the present invention, and became 8.2 mml after 2 week drinking of the tea drinks. During that period, in the first week, 50 mg of acarbose and pioglitazone was administrated with the first mouthful food and was stopped in the secondary week.

Case 46
 Patient: 59-year-old, male
 The tested fasting blood glucose value was 12 mml before drinking the traditional Chinese medicine tea drinks of the present invention, and became 8.0 mml after 2 week drinking of the tea drinks. During that period, in the first week, 50 mg of acarbose and pioglitazone was administrated with the first mouthful food and was stopped in the secondary week.

Case 47
 Patient: 57-year-old, male
 The tested fasting blood glucose value was 7 mml before drinking the traditional Chinese medicine tea drinks of the present invention, and became 5.9 mml after 2-week drinking of the tea drinks. During that period, in the first week, the subcutaneous injections of 8 units of insulin were performed before meals and stopped in the secondary week.

Case 48
 Patient: 47-year-old, male
 The tested fasting blood glucose value was 9.1 mml before drinking the traditional Chinese medicine tea drinks of the present invention, and became 6.7 mml after 2 week drinking of the tea drinks. During that period, in the first week, 50 mg of acarbose was administrated with the first mouthful food and was stopped in the secondary week.

The administration of the tea drinks of the present invention is absolutely effective for all the above 48 subjects of the diabetic clinical tests, and is even more effective than that of chemical medicines.

The effect of the tea drinks of the invention is even better in the situation where the subjects replace administration of the common diabetic chemical medicines such as insulin, acarbose, pioglitazone, glipizide, glimepiride, gliclazide, metformin etc.

A further advantage of the traditional Chinese medicine tea drinks of the present invention is its broad spectrum. Patients with differential sensitive to different chemical medicines can administrate the same traditional Chinese medicine tea drinks of the present invention.

A still further advantage of the traditional Chinese medicine tea drinks of the present invention is its low toxicity. Dark tea is a common drink which has been drunk for thousands of years in China and no toxicity and side effects are found. The dried tangerine peels has been used as an additive of tea drinks or a flavoring of Chinese food for hundreds of years, and shows no toxicity and side effects. The recorded history of Dark tea used as traditional Chinese medicine has at least 400 years. The history of using dried tangerine peels as traditional Chinese medicine has 2000 years or more, and "Er'chen medical soup" decoction invented by ZhangZhongjing, a famous doctor of the Eastern Han dynasty in China has ever been used since then and shows no toxicity responses according to the record. There are no records showing that the combined application of Dark tea and dried tangerine peels has toxicity and side effects.

Another advantage of the traditional Chinese medicine tea drinks of the present invention is the comprehensive effects thereof. Except for the good effect of blood glucose decreasing, the traditional Chinese medicine tea drinks of the present invention has effects of decreasing blood lipids, blood pressure and body weight.

It should be understood that it the components dosages in traditional Chinese medicine recipes can be modified to enhance therapeutic effects in certain aspects, or some other adjuvant or assistant components can be added to increase the main functions or add other therapeutic functions. Such modifications or variations known to the skilled in the art will fall within the scope of inventive concept of the present invention.

The invention claimed is:

1. A composition for treating diabetes, comprising a mixture of fermented dried tangerine peels and dark tea formed by joint secondary fermentation, wherein in said mixture, the fermented dried tangerine peels are 5 parts by weight to 30 parts by weight and the dark tea is 95 parts by weight to 70 parts by weight, and
wherein
said fermented dried tangerine peels are a blend of green, yellow-green and yellow-red tangerine peels, with a ratio of 30 parts by weight of said green tangerine peels, 35 parts by weight of said yellow-green tangerine peels and 35 parts by weight of said yellow-red tangerine peels, and said dark tea is a blend of tea leaves from wild tea trees and human-planted tea trees with a ratio of 10 parts by weight of wild tea leaves and 90 parts by weight of human-planted tea leaves.

2. The composition for treating diabetes according to claim 1, wherein in said mixture of fermented dried tangerine peels and dark tea, the fermented dried tangerine peels are 20 parts by weight, and the dark tea is 80 parts by weight.

3. The composition for treating diabetes according to claim 1, wherein said fermented dried tangerine peels are a mixture of variety of peels aged from 5 years to 15 years, or above 15 years.

4. The composition for treating diabetes according to claim 3, wherein said fermented dried tangerine peels are in a ratio of 35% weight percent of 5 to 6 year-old said dried tangerine peels, 25% weight percent 7 to 8 year-old said dried tangerine peels, 20% weight percent 9 to 10 year-old said dried tangerine peels, 12% weight percent 11 to 12 year-old said dried tangerine peels, 5% weight percent 13 to 14 year-old said dried tangerine peels, and 3% 15 or more year-old said dried tangerine peels.

5. The composition for treating diabetes according to claim 1, wherein said dark tea consists of at least one of Jinfu tea, Fu tea, Qianliang tea, Bailiang tea, and a combination thereof.

6. A method for preparing a composition that comprises a mixture of fermented dried tangerine peels and dark tea formed by joint secondary fermentation, wherein in said mixture, the fermented dried tangerine peels are 5 parts by weight to 30 parts by weight and the dark tea is 95 parts by weight to 70 parts by weight, and wherein said fermented dried tangerine peels are a blend of green, yellow-green and yellow-red tangerine peels, with a ratio of 30 parts by weight of said green tangerine peels, 35 parts by weight of said yellow-green tangerine peels and 35 parts by weight of said yellow-red tangerine peels, and said dark tea is a blend of tea leaves from wild tea trees and human-planted tea trees with a ratio of 10 parts by weight of wild tea leaves and 90 parts by weight of human-planted tea leaves, said method comprising:
- mixing 5 parts by weight to 30 parts by weight of dried tangerine peels with 95 parts by weight to 70 parts of pile-fermented black tea;
- pressing mixed dried tangerine peels and pile-fermented black tea into tea bricks; and
- undertaking a secondary fermentation of the tea bricks thereby forming said mixture of fermented dried tangerine peels and dark tea.

7. A composition comprising a mixture of fermented dried tangerine peels and dark tea formed by joint secondary fermentation, wherein in said mixture, the fermented dried tangerine peels are 5 parts by weight to 30 parts by weight and the dark tea is 95 parts by weight to 70 parts by weight, and wherein said fermented dried tangerine peels are a blend of green, yellow-green and yellow-red tangerine peels, with a ratio of 30 parts by weight of said green tangerine peels, 35 parts by weight of said yellow-green tangerine peels and 35 parts by weight of said yellow-red tangerine peels, and said dark tea is a blend of tea leaves from wild tea trees and human-planted tea trees with a ratio of 10 parts by weight of wild tea leaves and 90 parts by weight of human-planted tea leaves; and
- wherein said mixture of fermented dried tangerine peels and dark tea is obtained by:
  - mixing 5 parts by weight to 30 parts by weight of dried tangerine peels with 95 parts by weight to 70 parts of pile-fermented black tea;
  - pressing mixed dried tangerine peels and pile-fermented black tea into tea bricks; and
  - undertaking a secondary fermentation of the tea bricks thereby forming said mixture of fermented dried tangerine peels and dark tea.

8. The composition for treating diabetes according to claim 7, wherein in said mixture of fermented dried tangerine peels and dark tea, the fermented dried tangerine peels are 20 parts by weight, and the dark tea is 80 parts by weight.

9. The composition for treating diabetes according to claim 7, wherein said dark tea consists of at least one of Jinfu tea, Fu tea, Qianliang tea, Bailiang tea, and a combination thereof.

* * * * *